US00PP16171P2

(12) United States Plant Patent
Hofmann

(10) Patent No.: US PP16,171 P2
(45) Date of Patent: Dec. 20, 2005

(54) GERANIUM PLANT NAMED 'PACWU'

(50) Latin Name: *Pelargonium×hortorum*
Varietal Denomination: Pacwu

(75) Inventor: Christa Hofmann, Radeburg (DE)

(73) Assignee: Elsner pac Jungpflanzen, Dresden (DE)

( * ) Notice: Subject to any disclaimer, the term of this patent is extended or adjusted under 35 U.S.C. 154(b) by 0 days.

(21) Appl. No.: 11/000,446

(22) Filed: Nov. 30, 2004

(51) Int. Cl.[7] ..... A01H 5/00
(52) U.S. Cl. ..... Plt./329
(58) Field of Search ..... Plt./329, 325, 328

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Zonal Geranium plant named 'Pacwu', characterized by its upright and rounded plant habit; vigorous growth habit; freely branching and flowering habit; light purple-colored flowers with whitish centers arranged in rounded umbels held above and beyond the foliage on strong peduncles; and good garden performance.

1 Drawing Sheet

Botanical classification/cultivar designation: *Pelargonium×hortorum* cultivar Pacwu.

BACKGROUND OF THE INVENTION

The present invention relates to a new and distinct cultivar of Zonal Geranium plant, botanically known as *Pelargonium×hortorum*, and hereinafter referred to by the name 'Pacwu'.

The new Zonal Geranium is a product of a planned breeding program conducted by the Inventor in Dresden, Germany. The objective of the breeding program was to develop new Zonal Geraniums with vigorous growth habit and interesting flower and foliage colors.

The new Zonal Geranium originated from a cross-pollination made by the Inventor during the summer of 2000 of the *Pelargonium×hortorum*, cultivar Penblue, not patented, with an unknown seedling selection of *Pelargloniumxhortorum*, not patented. The cultivar Pacwu was discovered and selected by the Inventor as a flowering plant within the progeny from this cross-pollination in a controlled environment in Dresden, Germany in June, 2001.

Asexual reproduction of the new cultivar by terminal cuttings in a controlled environment in Dresden, Germany since January, 2002 has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'Pacwu'. These characteristics in combination distinguish 'Pacwu' as a new cultivar and distinguish it from other known Zonal Geranium cultivars:

1. Upright and rounded plant habit.
2. Vigorous growth habit.
3. Freely branching and flowering habit.
4. Light purple-colored flowers with whitish centers arranged in rounded umbels held above and beyond the foliage on strong peduncles.
5. Good garden performance.

Plants of the new Zonal Geranium can be compared to plants of the female parent, the cultivar Penblue. In side-by-side comparisons conducted in Dresden, Germany, plants of the new Zonal Geranium differed from plants of the cultivar Penblue in the following characteristics:

1. Plants of the new Zonal Geranium were more vigorous than plants of the cultivar Penblue.
2. Plants of the new Zonal Geranium flowered later than plants of the cultivar Penblue.
3. Plants of the new Zonal Geranium were more tolerant to rain and high temperatures than plants of the cultivar Penblue.

Plants of the new Zonal Geranium can be compared to plants of the cultivar Penlava U.S. Plant patent application Ser. No. 09/739,023, not patented. In side-by-side comparisons conducted in Dresden, Germany, plants of the new Zonal Geranium differed from plants of the cultivar Penlava in the following characteristics:

1. Plants of the new Zonal Geranium were more compact than plants of the cultivar Penlava.
2. Plants of the new Zonal Geranium were more freely branching than plants of the cultivar Penlava.
3. Plants of the new Zonal Geranium had lighter green-colored leaves and peduncles than plants of the cultivar Penlava.
4. Plants of the new Zonal Geranium and the cultivar Penlava differed slightly in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of a typical flowering plant of 'Pacwu' grown in a container.

DETAILED BOTANICAL DESCRIPTION

Plants of the cultivar Pacwu have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in 12-cm pots in Dresden, Germany, and grown under commercial practice in a glass-covered greenhouse with day temperatures averaging 18° C., night temperatures averaging 16° C. and light levels ranging from 15 to 100 kilolux. Plants used for the photograph and the detailed botanical description were about six months old. In the following description, color references are made to The Royal Horticultural Society Colour Chart, 1995 Edition, except where general terms of ordinary dictionary significance are used.

Botanical classification: *Pelargonium×hortorum* cultivar Pacwu.

Parentage:

*Female parent.*—*Pelargonium×hortorum* cultivar Penblue, not patented.

*Male parent.*—Unknown proprietary seedling selection of *Pelargonium×hortorum*, not patented.

Propagation:

*Type cutting.*—Terminal cuttings.

*Time to produce a rooted young plant.*—Summer: About 25 days at 22° C. Winter: About 30 days at 22° C.

*Root description.*—Fine, fibrous; white in color.

*Rooting habit.*—Freely branching, dense.

Plant description:

*General appearance.*—Upright and rounded plant habit; uniform; densely foliated.

*Growth and branching habit.*—Vigorous growth habit. Freely branching, about five lateral branches develop without pinching, that is, removal of terminal apices.

*Plant height, to top of umbels.*—About 25 cm.

*Plant height, to top of foliar plane.*—About 19 cm.

*Plant width.*—About 30 cm.

*Lateral branches.*—Length: About 10 cm. Diameter: About 7 mm. Internode length: About 2 cm. Texture: Pubescent. Strength: Moderately strong. Color: 145A.

*Foliage description.*—Arrangement: Alternate, simple. Length: About 4.5 cm. Width: About 8 cm. Shape: Reniform. Apex: Rounded. Base: Cordate; open or overlapping. Margin: Crenate. Venation pattern: Palmate. Texture, upper and lower surfaces: Pubescent. Color: Developing and fully expanded foliage, upper surface: 137A. Developing and fully expanded foliage, lower surface: 147B. Venation, upper surface: 137A. Venation, lower surface: 144A. Zonation pattern: Intensity: Weak. Width: About 2.5 cm. Color: Darker than 137A. Petiole: Length: About 6.5 cm. Diameter: About 3 mm. Texture, upper and lower surfaces: Pubescent. Color, upper and lower surfaces: 144A.

Flower description:

*Flower arrangement.*—Light purple-colored with whitish centers, flat, rotate and semi-double flowers arranged in rounded hemispherical umbels arising from apical leaf axils. Umbels displayed above the foliage on strong peduncles. Flowers face upright to outwardly. Umbels and flowers persistent. Flowers not fragrant.

*Quantity of flowers.*—Freely flowering habit; at full flower, plants have about ten open and developing umbels each with about 25 flowers and flower buds per umbel.

*Flowering season.*—Year-round under greenhouse conditions. In the garden in Dresden, Germany, flowering is continuous from April until frost in the fall.

*Flower longevity.*—Umbels flower for about three to four weeks on the plant.

*Umbel height.*—About 6 cm.

*Umbel diameter.*—About 11 cm.

*Flower diameter.*—About 5 cm.

*Flower depth (height).*—About 1 cm.

*Flower buds.*—Length: About 1.2 cm. Diameter: About 7 mm. Shape: Broadly elliptic. Color: 144A.

*Petals.*—Quantity per flower: About six. Length: About 2.5 cm. Width: About 2.5 cm. Shape: Obovate. Apex: Rounded. Base: Attenuate. Margin: Entire. Texture, upper and lower surfaces: Smooth, glabrous. Color: When opening, upper surface: 78B. When opening, lower surface: 75B. Fully opened, upper surface: 78C; towards the base, 69D; venation, 55B. Fully opened, lower surface: 75C; towards the base, 69D; venation, 55C.

*Sepals.*—Quantity per flower: Five, arranged in a single whorl. Length: About 1 cm. Width: About 3 mm. Shape: Lanceolate. Apex: Acute. Base: Cuneate. Margin: Entire. Texture, upper surface: Smooth, glabrous. Texture, lower surface: Pubescent. Color, upper and lower surfaces: 144A.

*Peduncle (umbel stem).*—Length: About 14 cm. Diameter: About 5 mm. Strength: Strong. Texture: Pubescent. Color: 144A.

*Pedicel (individual flower stem).*—Length: About 2.5 cm. Diameter: About 2 mm. Strength: Moderately strong. Texture: Pubescent. Color: 144A.

*Reproductive organs.*—Androecium: Anther quantity per flower: About nine. Anther length: About 2 mm. Anther shape: Elongated tube. Anther color: 182A. Pollen amount: Moderate. Pollen color: 171A. Gynoecium: Pistil quantity per flower: One. Pistil length: About 8 mm. Stigma shape: Spiral. Stigma color: 58A. Style length: About 3 mm. Style color: 55A. Ovary color: 138D.

*Seed/fruit.*—Seed and fruit development has not been observed.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind, and temperatures ranging from −0.5 to 40° C. and have demonstrated good garden performance.

It is claimed:

1. A new and distinct cultivar of Zonal Geranium plant named 'Pacwu', as herein illustrated and described.

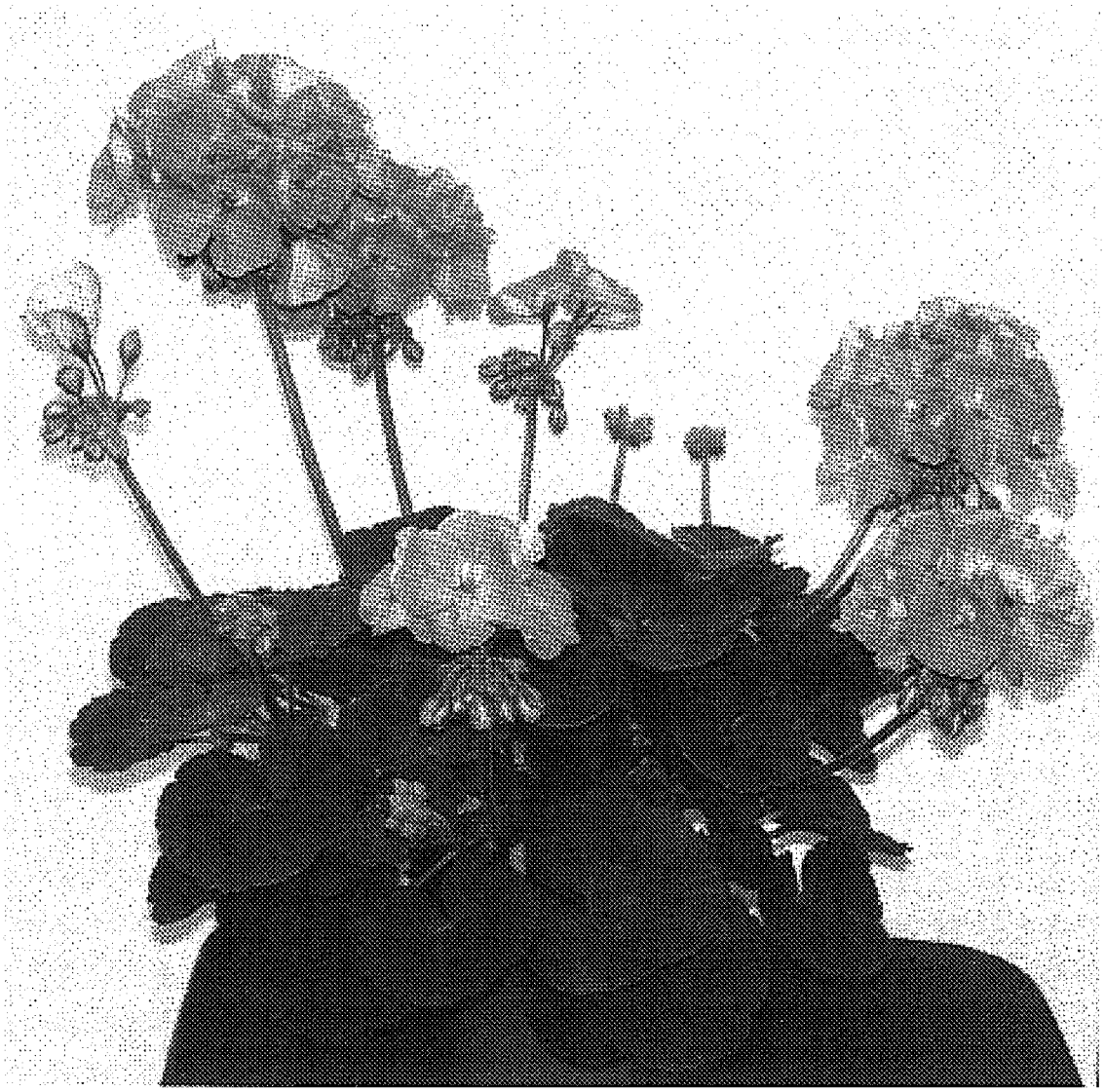

* * * * *